United States Patent [19]
Garrison et al.

[11] Patent Number: 5,607,302
[45] Date of Patent: Mar. 4, 1997

[54] MATRIX RETAINER APPARATUS FOR DENTAL RESTORATIONS

[76] Inventors: John E. Garrison, 18999 Sioux Dr.; Edgar L. Garrison, 17865 Oakwood Dr.; Robert Anderson, 113 Parkhurst Dr., all of Spring Lake, Mich. 49456

[21] Appl. No.: 518,801

[22] Filed: Aug. 24, 1995

Related U.S. Application Data

[63] Continuation-in-part of Ser. No. 323,874, Oct. 17, 1994, abandoned.

[51] Int. Cl.$^6$ .............................. A61C 5/04; A61C 3/00
[52] U.S. Cl. ..................... 433/39; 433/155; 433/162
[58] Field of Search ..................... 433/39, 139, 155, 433/149, 162; 606/156, 157, 158; 24/546, 564, 566

[56] References Cited

U.S. PATENT DOCUMENTS

| | | | |
|---|---|---|---|
| 532,723 | 1/1895 | Dennis . | |
| 644,705 | 3/1900 | Evans | 433/40 |
| 677,268 | 6/1901 | Power | 433/40 |
| 692,274 | 2/1902 | Gumaer | 24/564 |
| 867,379 | 10/1907 | Kaufmann | 24/261 |
| 2,083,077 | 6/1937 | Mayer | 24/83 |
| 2,088,208 | 7/1937 | Kassap | 24/261 |
| 2,567,101 | 6/1949 | Carpenter . | |
| 2,646,622 | 7/1953 | Christie et al. | 433/39 |
| 2,651,841 | 9/1953 | Peterson . | |
| 2,790,238 | 4/1957 | Trangmar . | |
| 3,074,169 | 1/1963 | Freeman | 433/162 X |
| 3,463,157 | 4/1969 | Hunt . | |
| 3,548,500 | 12/1970 | Cohen . | |
| 4,269,190 | 5/1981 | Behney . | |
| 4,303,389 | 12/1981 | Salsarulo | 433/40 |
| 4,824,365 | 4/1989 | von Weissenfluh | 433/40 |
| 4,986,752 | 1/1991 | Graves | 433/138 |

OTHER PUBLICATIONS

"Matrix Strips," Dental Products Report, May 1995, p. 6, no author.

*Primary Examiner*—Nicholas D. Lucchesi
*Attorney, Agent, or Firm*—Varnum, Riddering, Schmidt & Howlett LLP

[57] ABSTRACT

A matrix retainer apparatus for dental restorations is formed from a resilient, substantially planar main body, a pair of fines extending from the ends of the main body and retention members provided on the tines. The retention members serve to increase the coefficient of friction between the matrix retainer and the tooth or tooth reconstruction element and avoid inadvertent removal of the retainer therefrom. The invention is also directed to a matrix retainer system composed of several matrix retainers adapted for a variety of complex applications.

23 Claims, 1 Drawing Sheet

MATRIX RETAINER APPARATUS FOR DENTAL RESTORATIONS

RELATED APPLICATION INFORMATION

This is a continuation-in-part of U.S. patent application Ser. No. 08/323,874 filed Oct. 17, 1994 now abandoned.

BACKGROUND OF THE INVENTION

1. Field of the Invention

The present invention relates to dental implements. More specifically, it relates to a retaining aid for the metal contour band placed around a tooth when a proximalocclusal cavity in the tooth is to be filled. The device allows for improved contact between the contour band and the adjacent tooth which assures that the tooth worked upon will be in contact with the adjacent tooth after the cavity is filled. The retaining aid of the present invention has a generally arcuate and resilient main body with a pair of downward and inwardly depending tines or legs on each end. The distal ends of the legs can be slightly bulbous and may be coated or dipped in a substance imparting a high friction coefficient thereto. Optionally, the tips could be flattened or adapted to receive a disposable cover made of a rubber or like substance or simply have a bulbous tip in metal.

2. Description of the Prior Art

When the decayed portion of a tooth is located near the interproximal area between adjacent teeth, the most common way to guarantee that the filling properly conforms to the original shape of the tooth is to set a tooth reconstruction element, such as a thin band usually made of stainless steel or the like, about the tooth and secure it tightly thereto such that the band forms an outer shell or matrix that allows the filling material to harden in the correct shape. The present invention is an apparatus that aides the practitioner in retaining the matrix band in proper proximity to the tooth being worked upon. The resilience of the arcuate main body provides for the two depending legs to be urged inwardly toward one another to ensure a conforming matrix fit and also holds the retaining apparatus in place.

The depending legs can be of varying lengths to allow a plurality of the devices to be superimposed, one above the other, to allow for complex restoration processes or allows more than one tooth to be worked on at a time. A material providing a high frictional coefficient that can be coated onto the bulbous tips of the legs helps to prevent the apparatus from slipping and allows the device to be used with a variety of differently shaped teeth. A search at the U.S. Patent and Trademark Office uncovered a number of patents that relate to this invention, and they are discussed hereinafter.

First is U.S. Pat. No. 4,824,365 issued on Apr. 25, 1989 to Hans von Weissenfluh. This discloses a matrix in a flexible strip with an integral tightener. The flexible strip has two terminal extensions that are fastened to tabs extending from an annular tightener made of permanently deformable material. Thus, when the tightener is compressed, the flexible loop around the tooth is likewise tightened. This is dissimilar from the present invention in that there is no teaching of a separate flexible retainer with the depending legs.

In U.S. Pat. No. 4,303,389 issued on Dec. 1, 1981 to Angelo Salsarulo there is disclosed an instrument for the application of fillings. Though this discloses a matrix retainer that has an open end, there are no depending legs for engagement with the matrix.

U.S. Pat. No. 2,790,238 issued on Apr. 30, 1957 to Frank M. Trangmar discloses a dental matrix having a thicker, deformable portion to facilitate tightening the unit about the tooth to be worked on. Clearly, this is dissimilar from the present invention in that there is no resilient body with depending legs to aid in guaranteeing the interproximal contact between teeth after the filling has hardened.

U.S. Pat. No. 2,567,101 issued on Sep. 4, 1951 to Victor H. Carpenter discloses a matrix band for use in filling dental cavities. This band includes a spherical concavity located at a point thereon to allow for a rounded filling after hardening, thereby maintaining the proximal contact between the teeth. This is unlike the present invention in that no matrix retaining means is disclosed.

U.S. Pat. No. 3,548,500 issued on Dec. 22, 1970 to Theodore J. Cohen discloses a method of taking dental impressions. This is clearly dissimilar from the instant invention in that no separate retaining means for the matrix holder is taught.

U.S. Pat. No. 677,268 issued on Jun. 25, 1901 to Roscoe 0. Power discloses a dental instrument. This invention includes a horseshoe-shaped spring clamp to hold the matrix retainer in place, however there is no teaching of the depending legs and bulbous gripping tips of the present invention.

Lastly, U.S. Pat. No. 644,705 issued on Mar. 6, 1900 to George Evans discloses an impression band for dentistry. Projections are formed or soldered onto the side of the band ring and when the impression hardens, the ring is thus removed with the impression material. Contrast this to the present invention wherein depending legs apply pressure to the interproximal spaces bound by the matrix retainers.

None of the above inventions and patents, taken either singly or in combination, is seen to describe the instant invention as claimed.

SUMMARY OF THE INVENTION

The present invention is a substantially ting-shaped device with a pair of depending and converging legs on either of the distal ends. At the end of the depending legs, a slightly bulbous area is formed, and this area may be coated or otherwise sheathed in a substance which increases the frictional co-efficient of the leg end. Thus, the device may be spread by a tool and placed near the interproximal portion of a tooth that is being worked on to help retain the matrix band in place. The substance sheathing the bulbous leg ends helps to prevent the device from slipping or "popping off". It is contemplated that rings according to this invention could be made with a number of different leg lengths so that more than one could be set in place on either side of a tooth, allowing more than one restoration or one interproximal surface to be done at a time.

Accordingly, it is a major goal of the invention to provide a sectional matrix retainer for dental restorations that overcomes the disadvantages of the prior art.

Moreover, it is a principal object of the invention to provide a sectional matrix retainer for dental restorations wherein the depending and converging legs from the ring-shaped main body have bulbous tips which may be sheathed in a substance to increase the frictional coefficient and thus help prevent the retainer from inadvertently slipping off.

It is another object of the invention to provide a sectional matrix retainer for dental restorations wherein by varying the lengths of the depending legs, more than one ring may be placed about the teeth being worked on.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

The present invention meets or exceeds all the above objects and goals. Upon further study of the specification and appended claims, further objects and advantages of this invention will become apparent to those skilled in the art.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENT

Figure 4:
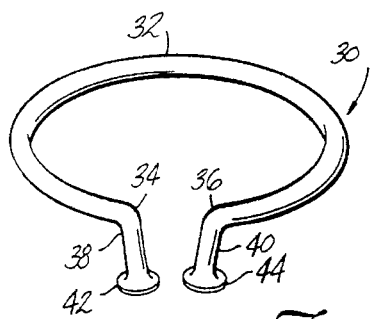
FIG. 4 is a front elevational view of a second embodiment of an improved matrix retainer apparatus according to the invention.

The first embodiment of a matrix retainer apparatus 10 according to the invention consists of a main body 12, that is generally ring shaped and lies in a plane Pl. Depending from either end of this ring shaped portion 12 are a pair of depending and converging tines or legs 14. The depending legs are of equal length, though it should be noted here that various lengths of these legs are contemplated to allow more than one retainer 10 to be used at a time. Thus will be discussed further hereinafter. At the end of each of the depending legs 14 of the first embodiment are knobs or bulbous tips 16. These bulbous tips 16 are smooth and assist in gripping the interproximal areas of the tooth being worked on, and thus retain that portion of the tooth reconstruction element or matrix 100 (seen in FIGS. 2 and 3) in close proximity to the desired shape. The tips 16 can be coated with a substance to increase the frictional coefficient of the surface to prevent the retainer apparatus 10 from slipping or popping off during the restoration procedure. As practitioners are well aware, this is a real problem during procedures with present art devices, leading to discomfort and annoyance to both the patient and the doctor. One such material that has been found to serve in this capacity is PLASTISOL, manufactured by Plast-o-meric Inc. located at 733 East Water Street, P.O. Box 247, North Baltimore, Ohio 45872. This is a PVC-based coating that increases the frictional coefficient sufficiently and has been shown to be able to stand up to the heat of an autoclave without degradation. The tips 16 of the device 10 are dipped in this material and allowed to dry. The material preferably used for the main body, legs, and tips of the invention would be stainless steel spring wire, although other materials could be used. Preferably, the wire is circular in cross section. Other methods of providing a higher frictional coefficient could be used, such as removable, disposable rubber sheaths that fit over the tips 16.

If the main body 12 is formed from spring wire, the resilience of the main body 12 tends to urge the legs 14 toward one another. Preferably, the spacing between the two legs 14 is less than the spacing between the opposed sides of a tooth to be restored. With the use of a suitable pair of dental pliers, the user can manipulate the ring 10 to increase the distance between the legs 14 (indicated by arrow A1 in FIG. 1) so that the legs can be placed across the buccolingual width of the interproximal tooth area in question (as seen in FIGS. 2 and 3) and the resilience of the main body 12 in conjunction with the bulbous tips 16 will maintain the device 10 in place and will also urge the retaining matrix into the correct shape.

The invention is also directed to a matrix restoration system whereby multiple rings 10 can be utilized for a wide variety of restoration processes and complex restoration processes. Experimentation has shown that rings having main body diameters of 0.675", 0.750", and 0.825" (inches) are suitable for the most common applications. In addition, the system includes rings having legs of differing length. One ring would have legs of a first prescribed length and the second ring would have legs greater than the first length. With this structure, the rings can be stacked one upon another, as described below, for complex restoration processes. Experimentation has shown that forming a first ring with legs which are 0.270" in length and a second ring with legs which are 0.370" (inches) in length are adaptable for a wide variety of restoration processes. The difference in leg length between the two rings can be as little as one millimeter and still achieve the overall advantages of the system. Preferably, the spacing between the depending legs is 0.10" (inches) with the dimensions being indicated at 24 in FIG. 1.

In use in a restoration of an occlusoproximal cavity (indicated at C in FIG. 3) in a tooth, a matrix band 100 is fitted to and placed around the tooth T that is to be worked on. To insure that the hardened filling, whether of the amalgam or composite resin type is of the correct shape, i.e. insuring proper contact between the cavity containing tooth and its neighbor, the present invention is manipulated by either a tool, i.e. a rubber dam forceps, in the direction indicated by arrow A1 in FIG. 1 spreading open the bulbous tips 16 and legs 14 so that the device 10 can be placed across the buccolingual width of the interproximal area of the two teeth, as can be clearly seen in FIGS. 2 and 3. The resilience of the main body 12 both holds the device 10 in place and also urges the matrix band 100 into the proper shape at the interproximal area to ensure that the adjacent teeth will maintain proper contact with one another after the filling has hardened. To aid in the separation and approximate the gingival portion of the tooth during the dental restoration process, a wedge W may be placed in the interproximal area in addition to the depending converging legs 14 of the device 10. The high frictional coefficient of the coating or sheath on the tip 16 is sufficient to prevent the inadvertent dislodgement of the device 10.

The utility of the differing lengths of the legs will now be discussed. Referring to FIG. 2, it can be seen that a pair of devices 10 can be superimposed that one with longer legs 14A can be placed on top of the one with shorter legs 14B. Thus, as seen in FIG. 3, if two interproximal carious tooth portions needed to be restored, the matrix 100 could be held at both interproximal areas to ensure proper fitting. It is contemplated even more of the retaining devices 10 could be used to allow for the dentist to perform three surface restorations at one time, both saving time, money, and patient discomfort.

Figure 1:
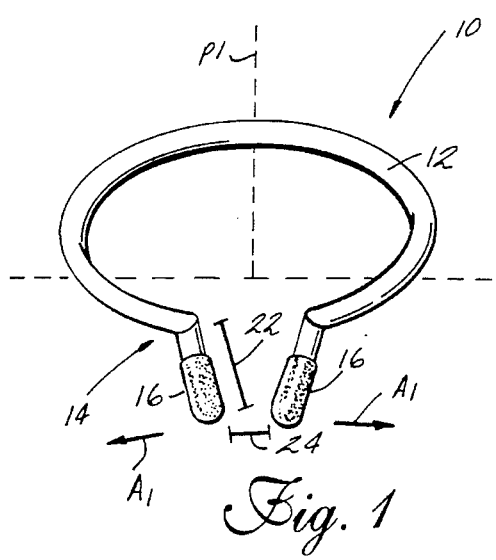
FIG. 1 is a front elevational view of a first embodiment of an improved matrix retainer apparatus according to the present invention showing the depending converging legs with the expanded or bulbous tips thereon.
Figure 2:
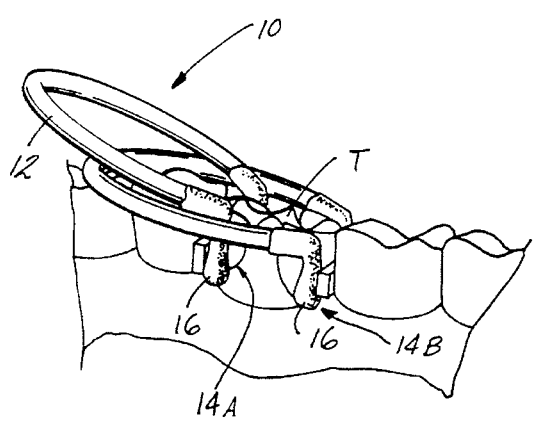
FIG. 2 is a side view of a dental restoration process showing the matrix retainer in place and with two of the retaining rings having differing leg lengths in place.
Figure 3:
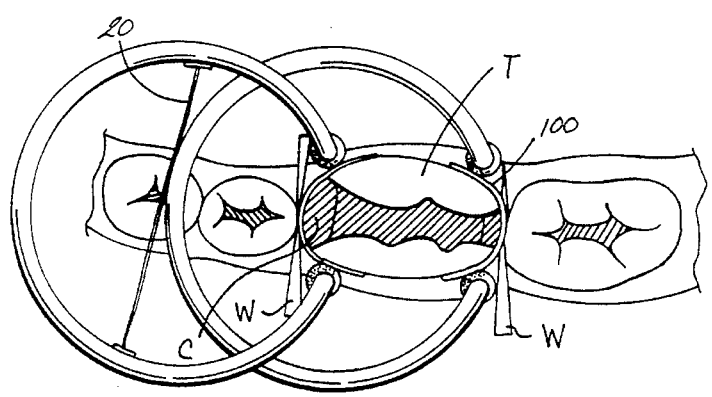
FIG. 3 is a top view of a similar restoration process to that seen in FIG. 2.

In the first embodiment seen in FIGS. 1–3, the legs 14 are coated with a suitable polymeric material such as heat-resistant vinyl and the like. FIG. 4 depicts another embodiment of the matrix retainer apparatus according to the invention. In this embodiment, the apparatus 30 comprises a retainer ring 32 having a pair of spaced apart ends 34, 36 and a pair of downwardly extending tines or legs 38, 40. The legs 38, 40 have a retainer member formed thereon to provide means for retaining the apparatus 30 on the tooth in the operative position. In this embodiment, the retainer member comprises a flattened head 42, 44 formed on the distal ends of the legs 38, 40. The flattened heads can be formed by any number of conventional processes. Preferably, the legs 38, 40 taper inwardly so that the spacing between the proximal ends of the two legs 38, 40 is greater than the spacing between the distal ends 42, 44 of the two legs 38, 40. This structure can be important in proper positioning of the device 10 on the matrix band 100 and the tooth being restored. Most teeth are bulbous in that the base is slightly narrower than the body of the tooth. The taper of the legs helps to accommodate the bulbous tooth structure and ensure that the distal ends of the device 10 tightly grip the matrix band 100 and hold it in place without interference from the body of the tooth. This creates an effective mechanical mounting of the device on the contoured tooth and matrix band. Preferably, the angle of taper of the legs is 7 degrees. However, a taper in the range of 4 to 30 degrees will achieve the above-stated advantages.

Figure 5:
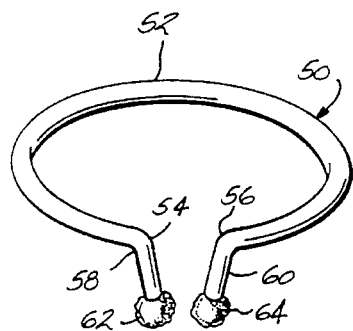
FIG. 5 is a front-elevational view of a third embodiment of an improved matrix retainer apparatus according to the invention.

FIG. 5 depicts a third embodiment of the matrix retainer apparatus according to the invention. In this embodiment, the retainer apparatus 50 comprises a retainer ring 52 with a pair of spaced apart ends 54, 56 and a pair of tines or legs 58, 60 depending from the ends 54, 56. In this embodiment, the retaining member comprises a roughened bulbous head 62, 64 provided at the distal end of the legs 58, 60. Preferably, the bulbous heads 62, 64 are formed by depositing or melting metal on the end by soldering, welding or some other metal forming process. In addition, the exterior surface of the heads 62, 64 are preferably roughened to enhance the coefficient of friction between the retaining member and the matrix band 100 when the apparatus 50 is in the operative position.

The matrix retainer apparatus according to the invention shows several different embodiments of retaining members provided on the legs of the apparatus. It is to be understood that any means for mechanically or structurally increasing the coefficient of friction between the legs and the band 100 and/or tooth T fall within the scope of the invention.

This system has been designed to adapt to various individual occlusal-gingival heights along with various bucco-lingual widths between molar-to-molar, molar-to-bicuspid, and primary-to-primary tooth contacts. The depending legs converging with one another allow for consistent placement about a wide variety of teeth without the concern that device could spring off.

It is to be understood that the present invention is not limited to the sole embodiment described above, but encompasses any and all embodiments within the scope of the following claims.

The embodiments for which an exclusive property or privilege is claimed are defined as follows:

1. A matrix retainer for dental restoration comprising:
    a resilient, substantially planar main body having a pair of spaced apart ends;
    a pair of tines, each time having a proximal end, a distal end, and a body intermediate the proximal and distal ends, the proximal ends being provided on the ends of the main body and the body and distal ends depending from the proximal ends so that the body and distal ends do not lie along the plane defined by the main body; and
    retention members provided on the distal ends of the tines, the retention members extending toward one another so that the spacing between the two retention members is less than the spacing between the proximal ends and bodies of the two tines wherein the resilient body and retention members are adapted to frictionally and mechanically retain and support a tooth reconstruction element in a fixed position relative to a tooth.

2. A matrix retainer according to claim 1 wherein at least one of the retention members comprises a flattened head.

3. A matrix retainer according to claim 1 wherein each retention member comprises a flattened head.

4. A matrix retainer according to claim 1 wherein at least one of the retention members comprises a bulbous head provided on at least one of the tines wherein the diameter of the bulbous head exceeds the diameter of the body of said at least one tine.

5. A matrix retainer according to claim 4 wherein bulbous heads are provided on both tines.

6. A matrix retainer according to claim 5 wherein the exterior surface of each bulbous head is roughened.

7. A matrix retainer according to claim 5 wherein each bulbous head is formed by a polymeric member.

8. A matrix retainer according to claim 7 wherein the polymeric member is formed from a high temperature polymer so that the retainer can be sterilized by autoclaving.

9. A matrix retainer according to claim 7 wherein the polymeric member is formed from a high temperature vinyl.

10. A matrix retainer according to claim 4 wherein the exterior surface of the bulbous head is roughened.

11. A matrix retainer according to claim 4 wherein the bulbous head is formed by a polymeric member provided on the tine.

12. A matrix retainer according to claim 1 wherein the body and the tines are circular in cross section.

13. A matrix retainer according to claim 1 wherein the resilient main body and the tines are formed from stainless steel spring wire.

14. A matrix retainer according to claim 1 wherein the tines are tapered so that the spacing between bodies of the tines adjacent the distal ends is less than the spacing between the proximal ends of the two tines.

15. A matrix retainer according to claim 14 wherein the angle of taper of the tines is in the range of 4 to 30 degrees.

16. A matrix retainer system for dental restoration comprising:
    a first retainer comprising:
        a resilient main body having a pair of spaced aparts ends;
        a first pair of tines depending from the spaced ends of the resilient main body wherein the tines have a first length, the tines being substantially perpendicular to a patient's gum line in the operative position; and
    a second retainer comprising:
        a resilient main body having a pair of spaced apart ends; and a second pair of tines depending from the spaced ends of the resilient main body wherein the second pair of tines have a second length which is greater than the first length of the first pair of tines, the second pair of times being substantially perpendicular to a patient's gum line in the operative position;

whereby both the first and second retainers can be used simultaneously in a dental restoration process with the second retainer in the operative position stacked on top of the first retainer.

17. A matrix retainer system according to claim 16 wherein the difference between the first and second tine lengths exceeds 1 mm.

18. A matrix retainer system according to claim 16 and further comprising a retention member provided on the tines wherein the resilient body and retention member are adapted to support and frictionally retain a tooth reconstruction element in a fixed position relative to a tooth.

19. A matrix retainer system according to claim 18 wherein the retention member comprises a flattened head formed on each tine.

20. A matrix retainer system according to claim 18 wherein the retention member comprises a bulbous head provided on each tine and the diameter of the head exceeds the diameter of its respective tine.

21. A matrix retainer adapted for use for dental restoration of a tooth, the matrix retainer comprising:

a resilient, substantially planar main body having a pair of spaced apart ends;

a pair of tines, each tine having a proximal end, a distal end, and a tine body intermediate the proximal and distal ends, the proximal ends being provided on the ends of the main body and the tine body and distal ends depending from the proximal ends so that the tine body and distal ends do not lie along the plane defined by the main body; and retention members provided on the distal ends of the tines, wherein each retention member comprises a bulbous head formed from a polymeric material and the resilient body and retention members are adapted to frictionally and mechanically retain and support a tooth reconstruction element on the tooth.

22. A matrix retainer according to claim 21 wherein the polymeric material is a high temperature polymer so that the retention members can be sterilized by autoclaving.

23. A matrix retainer according to claim 21 wherein the polymeric material comprises a high temperature vinyl.

* * * * *

UNITED STATES PATENT AND TRADEMARK OFFICE
CERTIFICATE OF CORRECTION

PATENT NO. : 5,607,302
DATED : March 4, 1997
INVENTOR(S) : JOHN E. GARRISON et al.

It is certified that error appears in the above-indentified patent and that said Letters Patent is hereby corrected as shown below:

Column 6, claim 1, line 6:
    "time" should be --tine--.

Signed and Sealed this

Eighth Day of July, 1997

*Attest:*

BRUCE LEHMAN

*Attesting Officer*      *Commissioner of Patents and Trademarks*